United States Patent [19]

Torelli et al.

[11] 4,154,730
[45] May 15, 1979

[54] NOVEL 17-SPIROSULTINES

[75] Inventors: Vesperto Torelli, Maisons-Alfort; Daniel Philibert, La Varenne Saint-Hilaire, both of France

[73] Assignee: Roussel Uclaf, Paris, France

[21] Appl. No.: 843,962

[22] Filed: Oct. 20, 1977

[30] Foreign Application Priority Data

Oct. 27, 1976 [FR] France .................. 76 32334

[51] Int. Cl.² .................. C07J 17/00; C07J 31/00
[52] U.S. Cl. .................. 260/239.5; 260/239.55 R; 260/239.55 C; 260/397.45; 424/241
[58] Field of Search .......... 260/239.5, 239.55, 397.45

[56] References Cited
U.S. PATENT DOCUMENTS 3,576,828   4/1971   Anner et al. .................. 260/397.3
3,971,777   7/1976   Rousseau et al. .......... 260/239.55 R Primary Examiner—Natalie Trousof
Assistant Examiner—Robert C. Whittenbaugh
Attorney, Agent, or Firm—Hammond & Littell

[57] ABSTRACT

Novel 17-spirosultines of steroids and the corresponding γ-hydroxy acids of the formula

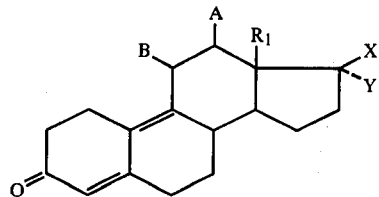

wherein $R_1$ is alkyl of 1 to 4 carbon atoms, A is hydrogen and B is hydrogen or hydroxyl of β configuration or A and B together form a double bond, X and Y together form the group

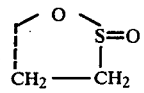

or X is -OH and Y is

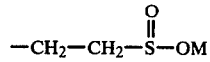

and M is selected from the group consisting of hydrogen, —NH₄ and an alkali metal having a remarkable progestomimetic and antialdosteronic activity and a novel process for their preparation and novel intermediates.

16 Claims, No Drawings

NOVEL 17-SPIROSULTINES

STATE OF THE ART

U.S. Pat. No. 3,971,777 and Belgium Pat. No. 852,457 describe 17-spirosultines of steroids which possess aldosterone antagonistic activity.

OBJECTS OF THE INVENTION

It is an object of the invention to provide the novel steroid derivatives of formula I.

It is another object of the invention to provide a novel process for the preparation of the compounds of formula I and novel intermediates produced therein.

It is a further object of the invention to provide novel antialdosteronic compositions with progestomimetic activity as well as a novel method of inducing progestomimetic and antialdosteronic activity in warm-blooded animals.

These and other objects and advantages of the invention will become obvious from the following detailed description.

THE INVENTION

The novel products of the invention have the formula

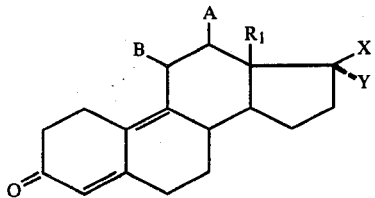

wherein $R_1$ is alkyl of 1 to 4 carbon atoms, A is hydrogen and B is hydrogen or hydroxyl of $\beta$ configuration or A and B together form a double bond, X and Y together form the group

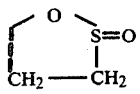

or X is —OH and Y is

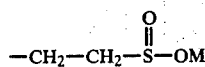

and M is selected from the group consisting of hydrogen, —NH$_4$ and an alkali metal. $R_1$ is preferably methyl or ethyl and examples of M as alkali metal are sodium, lithium or potassium.

The compounds exist in the form of two diastereoisomers on the level of the sulfur atom which may be separated in a known way. The isomers are named the A and B isomers and by convention, the A isomer is the isomer with the higher melting point. The racemic mixtures and the individual diastereoisomers are part of the invention.

Among the preferred groups of compounds of formula I are those wherein $R_1$ is methyl, those wherein X and Y are

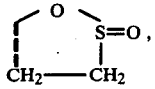

those wherein X is —OH and Y is

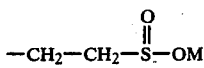

those wherein A and B are hydrogen, those wherein A is hydrogen and B is $\beta$—OH and those wherein A and B form a double bond.

Some specific preferred compounds of formula I are (17R) 2'-oxidospiro-[$\Delta^{4,9}$-estradiene-17,5'-(1',2')-oxathiolane]-3-ones, (17R) 2'-oxidospiro-[$\Delta^{4,9,11}$-estratriene-17,5'-(1',2')-oxathiolane]-3-ones and (17R) 2'-oxidospiro-[$\Delta^{4,9}$-estradiene-17,5'-(1',2')-oxathiolane]-11$\beta$-ol-3-ones.

The novel process of the invention for the preparation of a compound of formula I wherein X and Y form

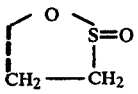

comprises reacting in the presence of an alkaline agent a compound of the formula

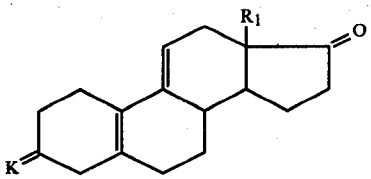

wherein K is a ketal group and $R_1$ is alkyl of 1 to 4 carbon atoms with a trimethylsulfonium halide of the formula $(CH_3)_3 S^+ Hal^-$ wherein Hal is a halogen to obtain a compound of the formula

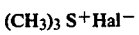

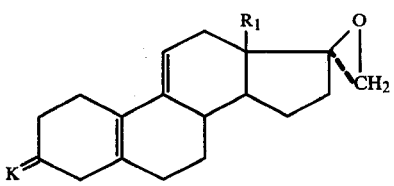

reacting the latter with methyltert.butylsulfoxide in the presence of butyllithium to obtain a compound of the formula

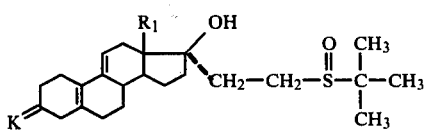

in the form of a mixture of diastereoisomers about the sulfur atom which can be separated, if desired, and either reacting the said product with an acid hydrolysis agent capable of hydrolyzing the ketal group while isomerizing the double bond system from $\Delta^{5(10), 9(11)}$ to $\Delta^{4,9}$ to obtain a compound of the formula

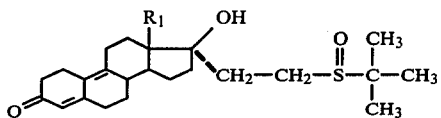

in the form of a diastereoisomer or a mixture thereof and reacting the product with N-bromosuccinimide or N-chlorosuccinimide to obtain a compound of the formula

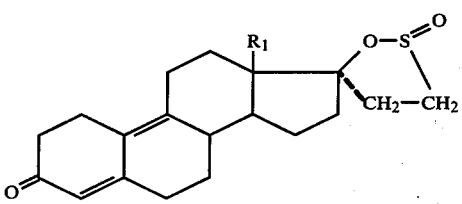

in the form of a diastereoisomer or a mixture thereof or reacting a compound of formula IV with an acid hydrolysis agent capable of hydrolyzing the ketal without isomerizing the double bond system to obtain a compound of the formula

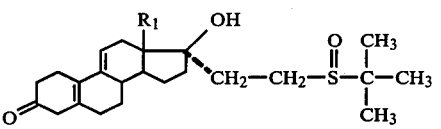

in the form of a diastereoisomer or a mixture thereof and reacting the latter either with a substituted parabenzoquinone to obtain a compound of the formula

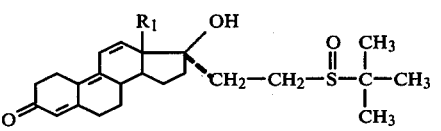

in the form of a diastereoisomer or a mixture thereof and then reacting the latter with N-bromosuccinimide or N-chlorosuccinimide to obtain a compound of the formula

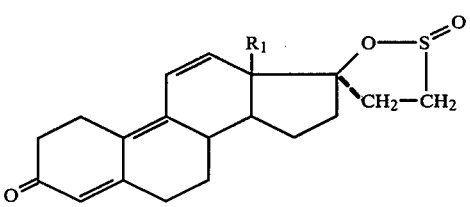

in the form of a diastereoisomer or a mixture thereof or reacting a compound of formula VI with a hydroperoxidation agent and then a reducing agent to obtain a compound of the formula

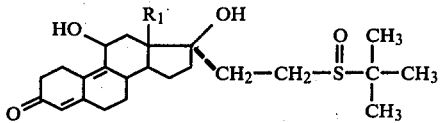

in the form of a diastereoisomer or a mixture thereof and reacting the latter with N-chlorosuccinimide or N-bromosuccinimide to obtain a compound of the formula

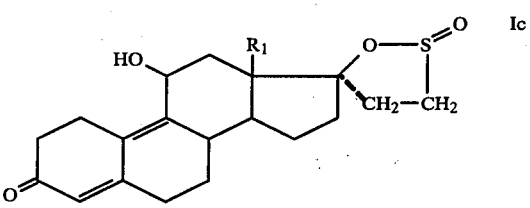

in the form of a diastereoisomer or a mixture thereof.

Preferably, the group K is a cyclic alkylketal of 2 to 4 carbon atoms such as ethyleneketal or propyleneketal as well as a dialkylketal such as dimethylketal or diethylketal. The trimethylsulfonium halide is preferably the bromide or the iodide and the alkaline agent is preferably sodium ethylate.

The acid hydrolysis agent capable of hydrolyzing the ketal group while isomerizing the $\Delta^{5(10), 9(11)}$ double bond system to the $\Delta^{4,9}$-system is preferably a mineral acid such as hydrochloric acid or sulfuric acid in a lower alkanol or perchloric acid in acetic acid or a sulfonic acid such as p-toluene sulfonic acid. The acid hydrolysis agent capable of hydrolyzing the ketal group without isomerizing the double bond system is preferably aqueous acetic acid.

The agent for forming the sultine is preferably N-chlorosuccinimide and the substituted p-benzoquinone is preferably 2,3-dichloro-5,6-dicyano-p-benzoquinone, 2,3-dibromo-5,6-dicyano-p-benzoquinone, 2,3,5,6-tetrachloro-p-benzoquinone, 2,3-dicyano-5-chloro-p-benzoquinone or 2,3-dicyano-p-benzoquinone. The reaction with the substituted p-benzoquinone is effected in a number of solvents and especially dioxane, methylenechloride, dichloroethane, benzene, toluene, ethyl acetate or propyl acetate.

The hydroperoxidation agent is preferably oxygen in the presence of an amine such as pyridine or triethylamine and the reducing agent for the hydroperoxide is preferably a trialkylphosphite such as triethylphosphite. The mixture of diastereoisomers obtained in the process may be separated by known methods such as chromatography.

In a preferred process of the invention, K is ethyleneketal and the trimethylsulfonium halide is the iodide and it is reacted in the presence of sodium ethylate. The acid hydrolysis agent capable of hydrolyzing the ketal and isomerizing the double bond system is perchloric acid in acetic acid and the cyclization agent for the spirosultine is N-chlorosuccinimide. The p-benzoquinone is 2,3-dichloro-5,6-dicyano-p-benzoquinone and the hydroperoxidation agent is oxygen in the presence of triethylamine and the reducing agent is triethylphosphite.

The process of the invention for the preparation of a compound of formula I wherein X is OH and Y is

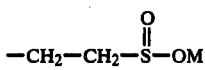

and M is hydrogen, —NH₄ or an alkali metal comprises reacting a compound of formula Ia, Ib or Ic with an alkali metal hydroxide or ammonium hydroxide to obtain a compound of formula I wherein M is —NH₄ or an alkali metal which may be reacted with an acidification agent to obtain a compound of formula I wherein M is hydrogen which may be reacted with an alkali metal base to form a compound of formula I wherein M is an alkali metal.

In a variation of the process of the invention, a compound of formula VIII in the form of a diastereoisomer or mixture thereof is reacted with a strong acid to obtain a compound of formula VII in the form of a diastereoisomer or a mixture thereof. The strong acid is preferably perchloric acid and the reaction is effected in an aprotic solvent such as methylene chloride, ether, chloroform or tetrahydrofuran or a mixture of one of the said solvents with acetonitrile.

The novel intermediates of the invention are the compounds of formulae III, IV, V, VI, VII and VIII.

The starting compounds of formula II are generally known and may be prepared by the process of French Pat. No. 1,336,083 which comprises reacting a compound of the formula

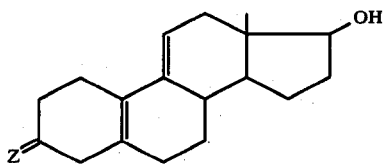

wherein Z is a ketal with an oxidizing agent.

The novel progestomimetic and antialdosteronic compositions of the invention are comprised of a progestomimetic and antialdoteronically effective amount of at least one compound of formula I and an inert pharmaceutical carrier or excipient. The compositions may be in the form of tablets coated tablets, cachets, capsules, granules, emulsions, syrups, suppositories and injectable solutions or suspensions.

The excipient may be those normally employed such as talc, arabic gum, lactose, starch, magnesium stearate, cacao butter, aqueous or non-aqueous vehicles, fatty bodies of animal or vegetable origin, paraffinic derivatives, glycols diverse wetting agents, dispersants or emulsifiers and preservatives.

The compositions are useful for the treatment of menstrual troubles due to luteal insufficiencies such as amenorrhea or metrorrhagia, primary or secondary sterility due to luteal insufficiencies without the undesired side effects due to aldosterone hypersecretion. The preferred compounds are (17R) 2'-oxidospiro-[Δ⁴,⁹-estradiene-17,5'-(1',2')-oxathiolane]-3-ones and (17R) 2'-oxidospiro-[Δ⁴,⁹,¹¹-estratriene-17,5'-(1',2')-oxathiolane]-3-ones.

The novel method of inducing progestomimetic and antialdosteronic activity in warm-blooded animals, including humans, comprises administering to warm-blooded animals a progestomimetically and antialdosteronically effective amount of at least one compound of formula I. The compounds may be administered orally, rectally, transcutaneously or intravenously and the usual useful dose is 0.002 to 2 mg/kg depending on the specific compound and the method of administration.

In the following examples there are described several preferred embodiments to illustrate the invention. However, it is to be understood that the invention is not intended to be limited to the specific embodiments.

EXAMPLE 1

B isomer of (17R) 2'-oxidospiro-[Δ⁴,⁹-estradiene-17,5'-(1',2')-oxathiolane]-3-one STEP A: 3-[(1,2-ethanediyl)-acetal] of (17R) spiro-Δ⁵⁽¹⁰⁾, ⁹⁽¹¹⁾-estradiene-17,2'-oxiran-3-one A solution of 5.25 g of trimethylsulfonium iodide in 50 ml of dimethylsulfoxide was added to a solution of 4.6 g of 3-[(1,2-ethanediyl)-acetal] of Δ⁵⁽¹⁰⁾, ⁹⁽¹¹⁾-estradiene-3,17-dione prepared by the procedure of French Pat. No. 1,336,083 in 15 ml of tetrahydrofuran and after cooling the mixture to 10° C., 2 g of sodium ethylate were added thereto with stirring. The mixture was stirred for one hour and 200 ml of water were added thereto. The mixture was extracted with ether and the ether extracts were washed with water, dried and evaporated to dryness to obtain 4.4 g of 3-[(1,2-ethanediyl)-acetal] of (17R) spiro-Δ⁵⁽¹⁰⁾,⁹⁽¹¹⁾-estradiene-17,2'-oxiran-3-one melting at 110° C. after crystallization from petroleum ether (b.p. = 60°–80° C.).

STEP B: A and B isomers of 3-[(1,2-ethanediyl)-acetal] of 21-(1,1-dimethylethylsulfinyl)-19-nor-17α-Δ⁵⁽¹⁰⁾,⁹⁽¹¹⁾-pregnadiene-17β-ol-3-one 20 ml of a solution of 2M of butyllithium in hexane were added over 30 minutes to a mixture of 4.7 g of tert. butyl methyl sulfoxide and 40 ml of tetrahydrofuran cooled to 0° to 5° C. and then a solution of 5.15 g of the product of Step A in 30 ml of tetrahydrofuran was added thereto. The temperature was allowed to rise to room temperature and the mixture stood for 22 hours. The mixture was diluted with water and was extracted with chloroform. The chloroform extracts were evaporated to dryness and the residue was chromatographed over silica gel. Elution with a 7-3 benzene-acetone mixture yielded successively 2.82 g of the A isomer of 3-[(1,2-ethanediyl)-acetal] of 21-(1,1-dimethylethylsulfinyl)-19-nor-17α-Δ⁵⁽¹⁰⁾,⁹⁽¹¹⁾-pregnadiene-17β-ol-3-one melting at 204° C. after crystallization from methyl ethyl ketone and having an Rf = 0.2 (7-3 benzene-acetone mixture) and then 2.99 g of the B isomer of the said product with a melting point of 116° C. after crystallization from 50% aqueous ethanol and having an Rf = 0.13 (7-3 benzene-acetone mixture).

STEP C: A isomer of 21-(1,1-dimethylethylsulfinyl)-19-nor-17α-Δ⁵⁽¹⁰⁾,⁹⁽¹¹⁾-pregnadiene-17β-ol-3-one A solution of 3 g of the A isomer of Step B in 30 ml of acetic acid and 3 ml of perchloric acid stood at room temperature for one hour and was then diluted with water. The mixture was extracted with chloroform and the organic extracts were evaporated to dryness. The residue was chromatographed over silica gel and was eluted with a 7-3 benzene-acetone mixture to obtain 2.38 g of the A isomer of 21-(1,1-dimethyl ethyl sulfinyl)-19-nor-17α-Δ⁵⁽¹⁰⁾,⁹⁽¹¹⁾-pregnadiene-17β-ol-3-one which was used as is for the next step. After crystallization from ethanol, the product melted at 256° C. and had a specific rotation of $[\alpha]_D^{20} = -317° \pm 4°$ (c = 1% in chloroform).

STEP D: isomer B of (17R) 2'-oxidospiro-[$\Delta^{4,9}$-estradiene-17,5'-(1',2')-oxathiolane]-3-one 764mg of N-chlorosuccinimide were added to a solution of 2.1 g of the A isomer of Step C in 40 ml of tetrahydrofuran and 20 ml of distilled water and the mixture was stirred at room temperature for 45 minutes. The tetrahydrofuran was removed by distillation under reduced pressure and the mixture was diluted with water and stirred for 30 minutes. The mixture was vacuum filtered and the recovered product was washed and dried to obtain 1.65 g of the B isomer of (17R) 2'-oxidospiro-[$\Delta^{4,9}$-estradiene-17,5'-(1',2')-oxathiolane]-3-one melting at 165° C. A sample crystallized from ethyl acetate melted at 174° C. and had a specific rotation of $[\alpha]_D^{20} = -353° \pm 4°$ (c = 1% in chloroform).

EXAMPLE 2

A isomer of (17R) 2'-oxidospiro-[$\Delta^{4,9}$-estradiene-17,5'-(1',2')-oxathiolane]-3-one

STEP A: B isomer of 21-(1,1-dimethylethylsulfinyl)-19-nor-17α-$\Delta^{4,9}$-pregnadiene-17β-ol-3-one Using the procedure of Step C of Example 1, 3.7 g of the B isomer of 3-[(1,2-ethanediyl)-acetal] of 21-(1,1-dimethylethylsulfinyl)-19-nor-17α-$\Delta^{5(10),9(11)}$-pregnadiene-17β-ol-3-one were reacted to obtain 2.56g of the B isomer of 21-(1,1-dimethylethylsulfinyl)-19-nor-17α-$\Delta^{4,9}$-pregnadiene-17β-ol-3-one melting at 174° C. after crystallization from ethyl acetate and a specific rotation of $[\alpha]_D^{20} = -172° \pm 2.5°$ (c = 1% in chloroform).

STEP B: A isomer of (17R) 2'-oxidospiro-[$\Delta^{4,9}$-estradiene-17, 5'-(1',2')-oxathiolane]-3-one Using the procedure of Step D of Example 1, 2.3 g of the product of Step A were reacted to obtain 1.13 g of the A isomer of (17R) 2'-oxidospiro-[$\Delta^{4,9}$-estradiene-17,5'-(1',2')-oxathiolane]-3-one melting at 217° C. and having a specific rotation of $[\alpha]_D^{20} = -281° \pm 4.5°$ (c = 1% in chloroform).

EXAMPLE 3

B isomer of (17R) 2'-oxidospiro-[$\Delta^{4,9,11}$-estratriene-17,5'-(1',2')-oxathiolane]-3-one

STEP A: A isomer of 21-(1,1-dimethylethylsulfinyl)-19-nor-17α-$\Delta^{5(10),9(11)}$-pregnadiene-17β-ol-3-one A mixture of 8 g of the A isomer of 3-[(1,2-ethanediyl)-acetal] of 21-(1,1-dimethylethylsulfinyl)-19-nor-17α-$\Delta^{5(10),9(11)}$-pregnadiene-17β-ol-3-one melting at 204° C. in 80 ml of acetic acid containing 25% water was stirred overnight at room temperature under an inert gas and was then diluted with water. The mixture was extracted with methylene chloride and the organic extracts were washed, dried and evaporated to dryness. The residue was chromatographed over silica gel and was eluted with a 7-3 benzene-acetone mixture to obtain the A isomer of 21-(1,1-dimethylethylsulfinyl)-19-nor-17α-$\Delta^{5(10),9(11)}$-pregnadiene-17β-ol-3-one with an Rf = 0.20.

STEP B: A isomer of 21-(1,1-dimethylethylsulfinyl)-19-nor-17α-$\Delta^{4,9,11}$-pregnatriene-17β-ol-3-one 4.1 g of 2,3-dichloro-5,6-dicyano-benzoquinone were added to a solution of the product of Step A in 120 ml of benzene and the mixture was stirred at room temperature for 15 minutes. The mixture was filtered to remove 2,3-dichloro-5,6-dicyano-parahydroquinone and the filtrate was washed with water, with a 0.1N sodium thiosulfate solution, with a sodium bicarbonate solution and then with water. The filtrate was dried and evaporated to dryness and the residue was chromatographed over silica gel. Elution with a 6-4 chloroform-acetone mixture yielded 2.75 g of the A isomer of 21-(1, 1-dimethylethylsulfinyl)-19-nor-17α-$\Delta^{4,9,11}$-pregnatriene-17β-ol-3-one with an Rf = 0.30.

STEP C: B isomer of (17R) 2'-oxidospiro-[$\Delta^{4,9,11}$-estratriene-17,5'-(1',2')-oxathiolane]-3-one A solution of 2.7 g of the product of Step B in 50 ml of tetrahydrofuran and 30 ml of water was stirred with 910 mg of N-chlorosuccinimide for 15 minutes and the pH of the solution was adjusted to 6–7 with a sodium bicarbonate solution. The mixture was diluted with water and was extracted with ethyl acetate. The organic phase was evaporated to dryness and the residue was chromatographed over silica gel. Elution with a 1-1 benzene-ethyl acetate mixture yielded 1.5 g of the B isomer of (17R) 2'-oxidospiro-[$\Delta^{4,9,11}$-estratriene-17,5'-(1',2')-oxathiolane]-3-one melting at 197° C. after crystallization from isopropanol and having a specific rotation of $[\alpha]_D^{20} = -215 \pm 4°$ (c = 0.5% in chloroform).

EXAMPLE 4

A isomer of (17R) 2'-oxidospiro-[$\Delta^{4,9,11}$-estratriene-17,5'-(1',2')-oxathiolane]-3-one

STEP A: B isomer of 21-(1,1-dimethylethylsulfinyl)-19-nor-17α-$\Delta^{5(10),9(11)}$-pregnadiene-17β-ol-3-one Using the procedure of Step A of Example 3, the B isomer of 3-[1,2-ethanediyl)-acetal] of 21-(1,1-dimethylethylsulfinyl)-19-nor-17α-$\Delta^{5(10),9(11)}$-pregnadiene-17β-ol-3-one melting at 116° C. was reacted to obtain the B isomer of 21-(1,1-dimethylethylsulfinyl)-19-nor-17α-$\Delta^{5(10),9(11)}$-pregnadiene-17β-ol-3-one which was chromatographed over silica gel. Elution with a 1-1 chlorform-acetone mixture yielded the product with an Rf = 0.35.

STEP B: B isomer of 21-(1,1-dimethylethylsulfinyl)-19-nor-17α-$\Delta^{4,9,11}$-pregnatriene-17β-3-one Using the procedure of Step B of Example 3, the product of Step A was reacted to obtain the B isomer of 21-(1,1-dimethylethylsulfinyl)-19-nor-17α-$\Delta^{4,9,11}$-pregnatriene-17β-ol-3-one with Rf = 0.25 (1-1 benzene-acetone mixture).

STEP C: A isomer of (17R) 2'-oxidospiro-[Δ⁴,⁹,¹¹-estratriene-17,5'-(1',2')-oxathiolane]-3-one Using the procedure of Step C of Example 3, the product of Step B was reacted to obtain the A isomer of (17R) 21-oxidospiro-[Δ⁴,⁹,¹¹-estratriene-17,5'-(1',2')-oxathiolane]-3-one which was chromatographed over silica gel and eluted with a 1-1 benzene-ethyl acetate mixture. After crystallization from ethyl acetate, the product melted at 200° C., then 212° C. and had a specific rotation $[\alpha]_D^{20} = -140.5° \pm 2.5°$ (c = 1% in chloroform).

EXAMPLE 5

B isomer of (17R) 2'-oxidospiro-[Δ⁴,⁹-estradiene-17,5'-(1',2')-oxathiolane]-11β-ol-3-one

STEP A: A isomer of 21-(1,1-dimethylethylsulfinyl)-19-nor-17α-Δ⁴,⁹-pregnadiene-11β,17β-diol-3-one 3.6 g of the A isomer of 21-(1,1-dimethylethylsulfinyl)-19-nor-17α-Δ⁵⁽¹⁰⁾,⁹⁽¹¹⁾-pregnadiene-17β-ol-3-one (prepared in Step A of Example 3) were dissolved in 120 ml of ethanol at room temperature and after the addition of 10 ml of triethylamine, oxygen was bubbled through the mixture for one hour. The solution was evaporated to dryness under reduced pressure and the residue was dissolved in 50 ml of ethanol. 1.65 ml of triethylphosphite was added to the solution which was then refluxed for one hour and then evaporated to dryness. The residue was chromatographed over silica gel and was eluted with a 1-1 chloroform-acetone mixture to obtain 2 g of the A isomer of 21-(1,1-dimethylethylsulfinyl)-19-nor-17α-Δ⁴,⁹-pregnadiene-11β, 17β-diol-3-one which melted at 256° C. after crystallization from a methanol-ethyl acetate mixture.

STEP B: B isomer of (17R) 2'-oxidospiro-[Δ⁴,⁹-estradiene-17, 5'-(1',2')-oxathiolane]-11β-ol-3-one A mixture of 760 mg of N-chlorosuccinimide and a solution of 2 g of the product of Step A in 40 ml of tetrahydrofuran and 20 ml of water was stirred at room temperature for 10 minutes and 5 ml of aqueous sodium bicarbonate solution were added thereto followed by 60 ml of a saturated sodium chloride solution. The mixture was extracted with ethyl acetate and the organic extracts were evaporated to dryness. The residue was chromatographed over silica gel and was eluted with a 1-1 benzene-acetone mixture to obtain 800 mg of the B isomer of (17R) 2'-oxidospiro-[Δ⁴,⁹-estradiene-17,5'-(1',2')-oxathiolane]-11β-ol-3-one which after crystallization from ethyl acetate melted at 221° C. and had a specific rotation of $[\alpha]_D^{20} = -92.5° \pm 2.5°$ (c = 0.5% in chloroform).

EXAMPLE 6

A isomer of (17R) 2'-oxidospiro-[Δ⁴,⁹-estradiene-17,5'-(1',2')-oxathiolane]-11β-ol-3-one

STEP A: 21-(1',1'-dimethylethylsulfinyl)-19-nor-17α-Δ⁴,⁹-pregnadiene-11β, 17β-diol-3-one (B isomer)

Using the procedure of Step A of Example 5, 3.2 g of the B isomer of 21-(1,1-dimethylethylsulfinyl)-19-nor-17α-Δ⁵⁽¹⁰⁾,⁹⁽¹¹⁾-pregnadiene-17β-ol-3-one were reacted to obtain 2.2 g of 21-(1,1-dimethylethylsulfinyl)-19-nor-17α-Δ⁴,⁹-pregnadiene-11β,17β-diol-3-one melting at 236° C. (B isomer)

STEP B: A isomer of (17R) 2'-oxidospiro-[Δ⁴,⁹-estradiene-17,5'-(1',2')-oxathiolane]-11β-ol-3-one Using the procedure of Step B of Example 5, 2.1 g of the product of Step A were reacted to obtain 1.5 g of the A isomer of (17R) 2'-oxidospiro-[Δ⁴,⁹-estradiene-17,5'-(1',2')-oxathiolane]-11β-ol-3-one. After crystallization from ethyl acetate, the product melted at 163° C. and had a sepcific rotation of $[\alpha]_D^{20} = -47° \pm 1.5°$ (c = 0.8% in chloroform).

EXAMPLE 7

Tablets were prepared containing 0.5 mg of the B isomer of (17R) 2'-oxidospiro-[Δ⁴,⁹-estradiene-17,5'-(1',2')-oxathiolane]-3-one and sufficient excipient of talc, starch and magnesium stearate for the tablet.

PHARMACOLOGICAL DATA

A. Progestomimetic Activity

The products tested were the B isomer of (17R) 2'-oxidospiro-[Δ⁴,⁹-estradiene-17,5'-(1',2')-oxathiolane]-3-one [product A] and the B isomer of (17R) 2'-oxidospiro-[Δ⁴,⁹,¹¹-estratriene-17,5'-(1',2')-oxathiolane]-3-one [product B] and the activity was determined by the method of hormonal receptors described by Raynaud et al [J. Ster. Biochem., Vol. 6 (1975), p. 615–622 and Physiology and Genetics of Reproduction, part A (1975), p. 143–160]. Impuberic rabbits received percutaneously 25 γ of estradiol and 5 days later, the animals were killed. The uterus was removed and homogenized in a buffered mixture of 10 mM of tromethamine, 0.25 M of saccharose and sufficient hydrochloric acid for a pH of 7.4. The homogenate was centrifuged at 105,000 g for one hour and the liquid surnageant or cytosol was adjusted to obtain a dilution of 1:50 (weight of uterus to volume).

The cytosol with a fixed concentration of tritiated 17,21-dimethyl-19-nor-Δ⁴,⁹-pregnadiene-3,20-dione (designated as tritiated product R) was incubated at 0° C. for 2 hours, in the presence or absence of increasing concentration of the same cold product (designated as cold product R), of progesternone or of the test product. At the end of 2 hours, the radioactivity of tritiated product R tied to the receptor was determined by the adsorption technique of carbondextran (1.25% to 0.625%).

The curves representing the percentages of tritiated product R tied with respect to the log of the concentration of the cold product R, progesterone or the test product added and that I₅₀ straight line parallel to axis of the abcisses and the ordinate of which is $$\frac{B}{T} = \frac{B/T \text{ max.} + B/T \text{ min.}}{2}$$

were drawn. B/T max. is the percentage of tritiated product R bound when no product was added and B/T min. is the percentage of tritiated product R bound when the maximum quantity of cold product R is added.

The intersections of line I₅₀ and the curves permit the determination of the CP and CX values. CP is the concentration of cold progesterone which inhibits by 50% the fixation of tritiated product R and CX is the concentration of test product which inhibits by 50% the fixation of tritiated product R. The relative affinity of the test product or RLA is determined by the formula $$RLA = 100 \times \frac{CP}{CX}$$

and the results are reported in Table I.

TABLE I

| Test Product | RLA |
|---|---|
| progesterone | 100 |
| A | 280 |
| B | 400 |

The results show that products A and B possess a progestomimetic activity from the biochemical view.

B. Antialdosteronic Activity In Rats

Male rats of the Sprague Dawley strain weighing about 180 g were subjected to surrenalectomy and at this moment, the rats received a drink of physiological serum. After about 2 days, the animals were fasted for 16 hours and then received a drink of an aqueous 5% glucose solution. The test products were administered subcutaneously at about 16 hours in the form of a solution or suspension in a 0.25% aqueous carboxymethyl cellulose solution containing Tween 80. One hour later, the animals received on the one hand intraperitoneally a hydrosaline surcharge at a dose of 5 ml/per rat of a 0.9% physiological serum and on the other hand subcutaneously 1 μg/kg of the monoacetate of aldosterone in a 2.5% alcoholic solution. The rats were placed in diuresis cages without food or drink for 4 hours and after this time, a forced urination was effected by pressure on the bladder. The volume of the obtained urine was adjusted to 50 ml and the amounts of sodium and potassium present was determined by an autoanalyzer. The results are expressed as a percentage of inhibition of the activity of 1 μg/kg of subcutaneously injected monoacetate of aldosterone by the ratio of sodium concentration to potassium concentration of the surrenalectomized rats. Product A had an 88% of inhibition at a dose of 5 mg/kg which indicates an interesting antialdosteronic activity.

Various modifications of the products and processes of the invention may be made without departing from the spirit or scope thereof and it is to be understood that the invention is intended to be limited only as defined in the appended claims.

We claim:

1. A compound of the formula

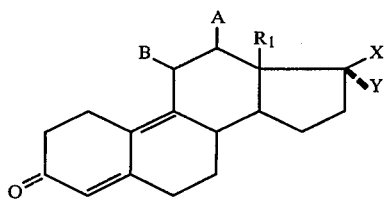

wherein $R_1$ is alkyl of 1 to 4 carbon atoms, A is hydrogen and B is hydrogen or hydroxyl of β configuration or A and B together form a double bond, X and Y together form the group

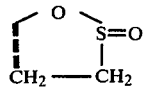

or X is —OH and Y is

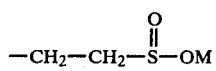

and M is selected from the group consisting of hydrogen, —NH₄ and an alkali metal.

2. A compound of claim 1 wherein $R_1$ is methyl.

3. A compound of claim 1 wherein X and Y form

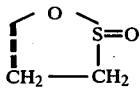

4. A compound of claim 1 wherein X is —OH and Y is

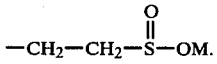

5. A compound of claim 1 wherein A and B are hydrogen.

6. A compound of claim 1 wherein A is hydrogen and B is β-OH.

7. A compound of claim 1 wherein A and B form a double bond.

8. A compound of claim 1 which is (17R) 2'-oxidospiro-[Δ⁴,⁹-estradiene-17,5'-(1',2')-oxathiolane]-3-ones.

9. A compound of claim 1 which is (17R) 2'-oxidospiro-[Δ⁴,⁹,¹¹-estratriene-17,5'-(1',2')-oxathiolane]-3-ones.

10. A compound of claim 1 which is (17R) 2'-oxidospiro-[Δ⁴,⁹-estradiene-17,5'-(1',2')-oxathiolane]-11β-ol-3-ones.

11. A process for the preparation of a compound of claim 1 wherein X and Y form

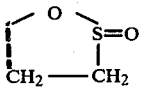

comprising reacting in the presence of an alkaline agent a compound of the formula

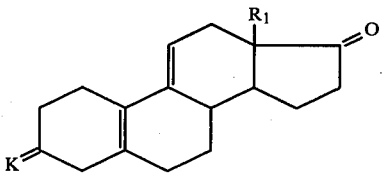

wherein K is a ketal group and $R_1$ is alkyl of 1 to 4 carbon atoms with a trimethylsulfonium halide of the formula (CH₃)₃S⁺Hal⁻ wherein Hal is a halogen to obtain a compound of the formula

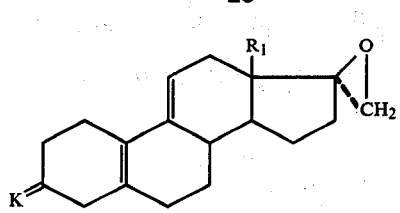

reacting the latter with methyltert.butyl sulfoxide in the presence of butyllithium to obtain a compound of the formula

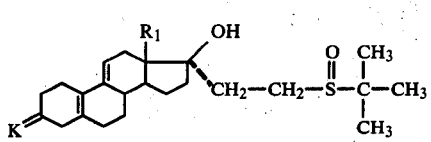

in the form of a mixture of diastereoisomers about the sulfur atom which can be separated, if desired, and either reacting the said product with an acid hydrolysis agent capable of hydrolyzing the ketal group and of isomerizing the double bond system from $\Delta^{5(10),9(11)}$ to $\Delta^{4,9}$ to obtain a compound of the formula

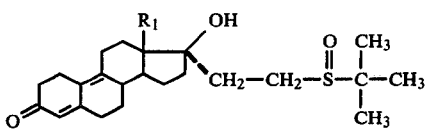

in the form of a diastereoisomer or a mixture thereof and reacting the product with N-bromosuccinimide or N-chlorosuccinimide to obtain a compound of the formula

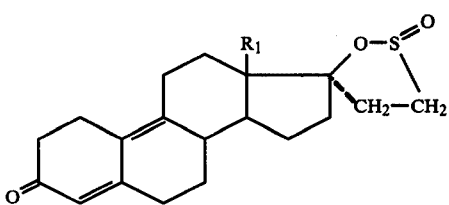

in the form of a diastereoisomer or a mixture thereof or reacting a compound of formula IV with an acid hydrolysis agent capable of hydrolyzing the ketal without isomerizing the double bond system to obtain a compound of the formula

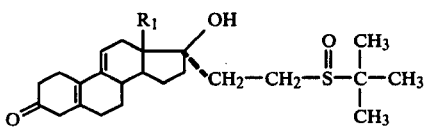

in the form of a diastereoisomer or a mixture thereof and reacting the latter either with a substituted para benzoquinone to obtain a compound of the formula

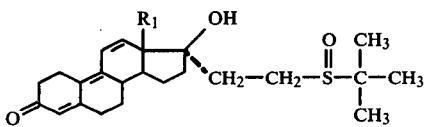

in the form of a diastereoisomer or a mixture thereof and then reacting the latter with N-bromosuccinimide or N-chlorosuccinimide to obtain a compound of the formula

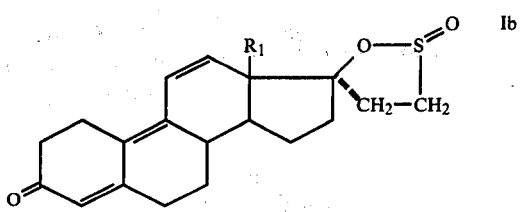

in the form of a diastereoisomer or a mixture thereof or reacting a compound of formula VI with a hydroperoxidation agent and then a reducing agent to obtain a compound of the formula

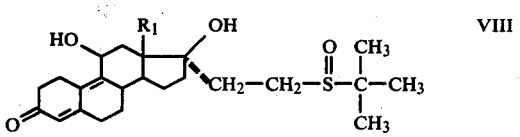

in the form of a diastereoisomer or a mixture thereof and reacting the latter with N-chlorosuccinimide or N-bromosuccinimide to obtain a compound of the formula

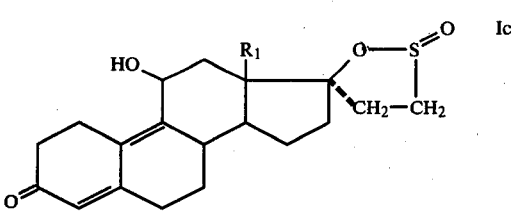

in the form of a diastereoisomer or a mixture thereof.

12. A progestomimetic and antialdosteronic composition comprising a progestomimetically and antialdosteronically effective amount of at least one compound of claim 1 and a pharmaceutical carrier.

13. A composition of claim 12 wherein $R_1$ is methyl.

14. A composition of claim 12 wherein the compound is selected from the group consisting of (17R) 2'-oxidospiro-[$\Delta^{4,9}$-estradiene-17,5'-(1',2')-oxathiolane]-3-ones and (17R) 2'-oxidospiro-[$\Delta^{4,9,11}$-estratriene-17,5'-(1',2')-oxathiolane]-3-ones.

15. A compound of a formula selected from the group consisting of

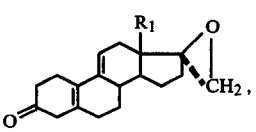

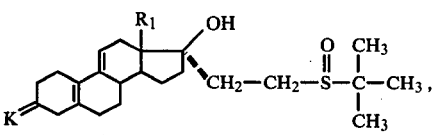

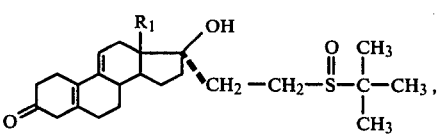

-continued
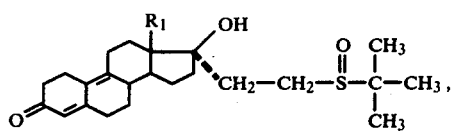
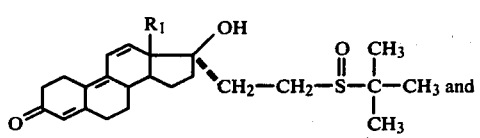
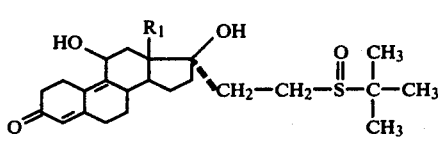
wherein $R_1$ is alkyl of 1 to 4 carbon atoms and K is a ketal.
16. A process for the preparation of a compound of the formula
wherein $R_1$ is alkyl of 1 to 4 carbon atoms comprising reacting a compound of the formula
with a strong acid.
* * * * *